(12) United States Patent
Baker et al.

(10) Patent No.: US 10,893,037 B2
(45) Date of Patent: Jan. 12, 2021

(54) MEDICAL DEVICE WIRELESS ADAPTER

(71) Applicant: Welch Allyn, Inc., Skaneateles Falls, NY (US)

(72) Inventors: Steven D. Baker, Beaverton, OR (US); Eric G. Petersen, Aloha, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 369 days.

(21) Appl. No.: 14/954,023

(22) Filed: Nov. 30, 2015

(65) Prior Publication Data

US 2016/0080365 A1 Mar. 17, 2016

Related U.S. Application Data

(62) Division of application No. 11/610,952, filed on Dec. 14, 2006, now abandoned.

(Continued)

(51) Int. Cl.
| | |
|---|---|
| *H04L 29/06* | (2006.01) |
| *A61B 5/0205* | (2006.01) |
| *A61B 5/00* | (2006.01) |
| *A61B 5/11* | (2006.01) |
| *G06F 19/00* | (2018.01) |
| *G16H 40/40* | (2018.01) |
| *H04L 29/08* | (2006.01) |
| *H04W 4/18* | (2009.01) |

(Continued)

(52) U.S. Cl.
CPC ........ *H04L 63/0823* (2013.01); *A61B 5/0002* (2013.01); *A61B 5/02055* (2013.01); *A61B 5/1113* (2013.01); *G06F 19/3418* (2013.01); *G16H 40/40* (2018.01); *H04L 63/083* (2013.01); *H04L 67/28* (2013.01); *H04L 69/16* (2013.01); *A61B 5/0015* (2013.01); *A61B 5/0022* (2013.01); *A61B 5/0024* (2013.01); *A61B 5/021* (2013.01); *A61B 5/024* (2013.01); *A61B 5/0402* (2013.01); *A61B 5/0476* (2013.01); *A61B 5/145* (2013.01); *A61B 5/746* (2013.01); *A61B 2560/0209* (2013.01); *A61B 2560/045* (2013.01); *G16H 10/65* (2018.01); *H04L 29/06* (2013.01); *H04L 69/00* (2013.01); *H04W 4/18* (2013.01); *H04W 88/04* (2013.01); *Y02D 30/70* (2020.08); *Y10S 128/92* (2013.01); *Y10S 439/909* (2013.01)

(58) Field of Classification Search
CPC ... A61B 5/0024; A61B 5/0002; A61B 5/0402; A61B 5/0006; A61B 5/0022; A61B 5/0205; A61B 5/14551; A61B 5/145; A61B 5/746; A61B 5/0015; A61B 5/72; G06F 19/3418; G06F 19/30; H04L 29/06; H04L 69/16; H04L 69/00; H04W 88/04; Y10S 128/92; Y10S 439/909
See application file for complete search history.

(56) References Cited

U.S. PATENT DOCUMENTS

| | | |
|---|---|---|
| 3,810,102 A | 5/1974 | Parks, III et al. |
| 5,387,994 A | 2/1995 | McCormack et al. |

(Continued)

*Primary Examiner* — Christian Jang
*Assistant Examiner* — Karen E Toth
(74) *Attorney, Agent, or Firm* — Barclay Damon LLP

(57) ABSTRACT

The invention relates generally to a medical device wireless adapter, and more particularly, to a module that adapts an existing legacy or newly designed medical device to a healthcare provider's wireless infrastructure.

18 Claims, 6 Drawing Sheets

Related U.S. Application Data

(60) Provisional application No. 60/750,202, filed on Dec. 14, 2005.

(51) Int. Cl.
| | |
|---|---|
| *A61B 5/0476* | (2006.01) |
| *A61B 5/0402* | (2006.01) |
| *A61B 5/021* | (2006.01) |
| *A61B 5/145* | (2006.01) |
| *A61B 5/024* | (2006.01) |
| *G16H 10/65* | (2018.01) |
| *H04W 88/04* | (2009.01) |

(56) References Cited

U.S. PATENT DOCUMENTS

| | | | | |
|---|---|---|---|---|
| 5,502,726 A * | 3/1996 | Fischer | ............... | H04L 12/28 |
| | | | | 370/392 |
| 5,938,733 A * | 8/1999 | Heimsoth | ............... | H04L 29/06 |
| | | | | 709/230 |
| 5,999,294 A | 12/1999 | Petsko | | |
| 6,047,207 A * | 4/2000 | MacDuff | ............... | G01D 9/005 |
| | | | | 600/510 |
| 6,138,186 A * | 10/2000 | Simms | ............... | G06F 3/0613 |
| | | | | 710/34 |
| 6,561,978 B1 * | 5/2003 | Conn | ............... | A61B 5/0031 |
| | | | | 600/309 |
| 6,616,606 B1 | 9/2003 | Petersen et al. | | |
| 6,650,939 B2 | 11/2003 | Taepke, II et al. | | |
| 6,763,032 B1 * | 7/2004 | Rabenko | ............... | H04L 1/0003 |
| | | | | 370/442 |
| 6,850,788 B2 | 2/2005 | Al-Ali | | |
| 6,876,958 B1 | 4/2005 | Chowdhury et al. | | |
| 6,950,859 B1 | 9/2005 | Bartek et al. | | |
| 7,129,836 B2 | 10/2006 | Lawson et al. | | |
| 7,321,599 B1 * | 1/2008 | Yen | ............... | H04W 4/18 |
| | | | | 370/466 |
| 7,382,247 B2 | 6/2008 | Welch et al. | | |
| 7,913,300 B1 | 3/2011 | Flank et al. | ............... | 726/12 |
| 2002/0016719 A1 * | 2/2002 | Nemeth | ............... | G06Q 50/22 |
| | | | | 705/2 |
| 2003/0016738 A1 * | 1/2003 | Boolos | ............... | H04L 1/24 |
| | | | | 375/224 |
| 2003/0065536 A1 * | 4/2003 | Hansen | ............... | A61B 5/14532 |
| | | | | 705/2 |
| 2003/0181798 A1 * | 9/2003 | Al-Ali | ............... | A61B 5/02438 |
| | | | | 600/324 |
| 2004/0137942 A1 * | 7/2004 | Lee | ............... | H04N 7/18 |
| | | | | 455/556.1 |
| 2004/0176667 A1 | 9/2004 | Mihai et al. | ............... | 600/300 |
| 2004/0199706 A1 * | 10/2004 | Phelps | ............... | G06F 12/0661 |
| | | | | 710/306 |
| 2004/0223180 A1 | 11/2004 | Brooks | ............... | 358/1.15 |
| 2004/0249999 A1 * | 12/2004 | Connolly | ............... | A61B 5/0002 |
| | | | | 710/33 |
| 2005/0015516 A1 | 1/2005 | Ju | | |
| 2005/0019848 A1 * | 1/2005 | Lee | ............... | A61B 5/0002 |
| | | | | 435/14 |
| 2005/0033148 A1 | 2/2005 | Haueter et al. | ............... | 600/407 |
| 2005/0091483 A1 * | 4/2005 | Fascenda | ............... | H04L 9/3234 |
| | | | | 713/153 |
| 2005/0165323 A1 | 7/2005 | Montgomery et al. | ........ | 600/544 |
| 2005/0237049 A1 * | 10/2005 | Ozaki | ............... | G01R 15/202 |
| | | | | 324/117 H |
| 2005/0261559 A1 | 11/2005 | Mumford et al. | ............ | 600/300 |
| 2006/0122542 A1 * | 6/2006 | Smith | ............... | A61B 5/0002 |
| | | | | 600/595 |
| 2006/0238333 A1 | 10/2006 | Welch et al. | | |
| 2007/0069887 A1 | 3/2007 | Welch et al. | | |
| 2008/0139953 A1 | 6/2008 | Baker et al. | | |

\* cited by examiner

MEDICAL DEVICE WIRELESS ADAPTER

CROSS-REFERENCE TO RELATED APPLICATIONS

This patent application is a divisional application of, and claims priority and benefit to, co-pending U.S. patent application Ser. No. 11/610,952, filed Dec. 14, 2006 and entitled "Medical Device Wireless Adapter", which is a non-provisional application of U.S. provisional patent application Ser. No. 60/750,202, filed Dec. 14, 2005 and entitled "Body Medical Device Wireless Adapter". All of the aforementioned patent(s) and patent application(s) are herein incorporated by reference in their entirety.

FIELD OF THE INVENTION

This invention relates generally to a medical device wireless adapter, and more particularly, to a module that adapts an existing legacy or newly designed medical device to a healthcare provider's wireless infrastructure.

BACKGROUND OF THE INVENTION

A broad range of existing and newly developed medical devices have a need for wireless connectivity. Such medical devices range from complex medical instrumentation incorporating embedded computers, including patient diagnostic equipment and patient monitors, to so-called "dumb" instruments that are network-unaware, such as a simple electronic thermometer with a serial output port that might do little more than make one type of measurement and output digital data representing the measurement.

The WiFi (Wireless-Fidelity) Alliance is an industry consortium that follows the IEEE 802.11 series of standards and works to improve interoperability between different suppliers. WiFi branded devices have become very popular and these devices are widely available. Connection or access points are also numerous, especially in more populated areas. Because of the proliferation of 802.11 computing devices, where physical proximity is not a barrier to network access, security is a concern. Encryption is one aspect of secure wireless operation. Wired Equivalent Privacy (WEP), the first type of 802.11 encryption, was defeated relatively quickly. WEP serves as an example of the potential vulnerability of wireless networks. TKIP and 802.11i (branded as WiFi Protected Access (WPA) and WPA2, respectively) have replaced WEP and are the standard encryption solutions in use today.

Medical 802.11 users must further comply with security requirements of the Health Information Portability and Accountability Act of 1996 (HIPAA). HIPAA mandates that healthcare providers take reasonable measures to maintain an environment and infrastructure where patient medical information is only disclosed to those people and entities that have a valid need to access this information. Accordingly, healthcare providers expect medical device manufacturers to provide medical instrumentation that operates within a healthcare infrastructure in a secure manner, without an unreasonable configuration and maintenance overhead.

As the HIPAA guidelines are being implemented, the Industrial, Scientific, and Medical (ISM) 802.11 radio band market has transitioned from an "early adopter" phase in circa 2000 to a stage where WiFi networks are commonly available. While adoption of these network standards has been widely viewed as successful and deployments are widespread (including healthcare institutions), initial mechanisms provided by these standards for managing a secure network have been proven to be vulnerable. The Institute of Electrical and Electronics Engineers (IEEE) and other organizations have responded with a number of significant improvements. Their efforts have produced a new set of standards for wireless authentication and encryption, which have benefited from extensive review and involvement by the cryptography community. This work has resulted in a two stage release, with TKIP (WPA) first addressing improved authentication and key exchange in legacy wireless hardware, and 802.11i (WPA2) providing full strength AES encryption, strong authentication, and highly robust key exchange protocols that provide even stronger security for new hardware designs. Legacy devices, as used herein, refer to medical, industrial, or scientific devices that do not have means for wirelessly connecting to a network and/or devices that do not support adequate authentication/encryption levels.

WPA and WPA2 take advantage of Public Key Cryptography, and provide a robust solution to the security problem. However, commercial products that implement these standards rely on the host processor in a PDA, laptop or desktop computer to implement the computationally intensive Public Key portions of these standards. When these products are applied to the types of Medical Devices introduced above, this places an enormous computational burden on a real-time processor that is generally not well suited to the task. While chip manufacturers typically develop drivers and supplicants for common operating systems and microprocessors, these are generally not available for embedded platforms. Porting this sizable set of functionality to a broad range of processors and real-time operating systems (RTOS) for a diverse set of medical devices presents a significant development and computational burden that impacts each of the products that need wireless connectivity. While modern object oriented design practices do help alleviate the development burden, porting code is still a manual process. Many of these legacy medical devices simply do not have the CPU or memory resources necessary to accommodate Public Key Cryptography. In the case of a network-unaware medical instrument, there are likely no available computational resources within the medical device to assist in any aspect of wireless connectivity. What is needed is a medical WiFi adapter that can accomplish authentication, key negotiation, certificate management and strong encryption without the involvement of a host computer or host medical device processor and without needing an external software library, such as a dynamic linked library (DLL), resident outside of the medical WiFi adapter related to the authentication, key negotiation, or certificate management functions.

Bi-directional authentication of a device using Certificates can protect both the device and the infrastructure from adversaries. What is needed is a robust bidirectional authentication system for use by medical devices on a WiFi healthcare network infrastructure. Since some healthcare infrastructures support only unidirectional authentication (verifying to the network that the device is allowed, but the device can't determine whether it is connected to an imposter network or the real network), what is also needed is a bi-directional authentication capable WiFi medical device wireless adapter that can also support unidirectional authentication. Configuring medical devices on a medical network, particularly if authentication is used, can be a daunting and time consuming process as every device must be manually configured. Therefore, what is also needed is a WiFi medical device wireless adapter that can manage available certificates and automatically present a series of certificates to an authentication server in an order in which they are most likely to be accepted. Even if many clients use strong authentication and encryption, when some client devices do not, unauthorized devices may access the network, leaving it vulnerable unless the network is carefully designed.

Another problem in adding a network-unaware medical device to a medical network involves defining the instrument and its control and measurement parameters and presenting them in a meaningful way to the medical network. What is needed is a medical WiFi adapter that can assign a unique identifier to each network-unaware medical device or instrument added to a medical network to give context to the wireless communications with each network-unaware device.

Another problem in adding wireless connectivity to a medical device is power consumption. Typical WiFi devices (including cards, boards, and modules), such as those available for laptops, involve a great deal of traffic while a user is interacting with a computer, surrounded by long periods of no activity. To conserve energy, users may disable the wireless interface. Even without this, laptop and PDA users can work within a process where the battery is charged every few hours. Medical devices operate with a completely different set of use models. For example, in one common medical device mode, the medical device needs to send relatively small packets of data to the network continuously, hour after hour, day after day without tying the patient to a power cord umbilical. WiFi products that have been developed for the laptop and general purpose computer market lack the power options needed for the typical modes of operation used by wireless medical devices and do not support the complexities of state of the art medical-grade wireless devices and networks. What is needed is a WiFi medical device wireless adapter that can support power options needed for the typical modes of operation of medical devices.

Another problem with commercial WiFi products is personal radio frequency (RF) safety. While there is no credible or definitive evidence to date regarding any cancer or similar human pathology caused by RF exposure, it is well known and accepted that radiated RF energy of sufficient power and duration can heat human tissue. In response to the intense interest of recent years generated by studies involving cell phones and human exposure to RF, the FCC has set standards for maximum exposure to RF. The FCC defines the quantity used to measure how much RF energy is actually absorbed in a body as the Specific Absorption Rate (SAR), expressed in units of watts per kilogram (W/kg) or milliwatts per gram (mW/g) for portable devices (used within 20 cm of the body). Commercial WiFi devices are designed for mobile products and therefore subject to the much less stringent Maximum Permissible Exposure (MPE) limits. Thus commercial 802.11 devices set their output RF power and duty cycle (ratio of transmit time to non-transmit time) based on communications performance parameters and requirements, generally ignoring SAR (and MPE) limits. A medical WiFi adapter might be used in conjunction with a medical device situated very close to a patient. If a WiFi device were to be situated very close to a human body for extended periods of time, it is possible that the RF power and/or the duty cycle of the WiFi device would need to be reduced to meet the FCC SAR requirements in such a way as to not impact the operation of the medical device. Therefore what is needed is a medical WiFi adapter that can avoid exceeding the FCC SAR limit, while not adversely impacting the operation of the medical device, even when situated or worn very close to a patient's body.

There currently exist methods to track the physical location of an actively communicating commercial WiFi device. However, these methods require ongoing communications operations of the commercial WiFi device and if the commercial WiFi device is set to a power save mode where the transceiver is inactive, tracking ceases. There also exist WiFi location tags, also know as asset tags or location beacons that can operate at low power or go to standby and periodically send out a short WiFi communication solely for the purposes of radio tracking. What is needed is a medical WiFi adapter having a plurality of operating modes that can operate both during active WiFi data communications and when the medical WiFi adapter is in a power saving state. What is further needed is a medical WiFi adapter that can continue to provide a tracking function even when the power is removed from any host medical device or computer to which it is attached.

Most commercially available WiFi devices include one antenna permanently affixed to the device, usually in the form of an antenna extension on a plug in WiFi computer card. At least one specialty WiFi device offers an antenna "pig tail", a short length of shielded RF cable with a connector to receive a cable from a WiFi antenna. However, what is needed is a medical WiFi adapter with two or more diversity antenna connections where the antennas can be located apart from each other and the antennas can be operated one at a time to aid in signal acquisition and asset location by RF beacon tracking.

There also exist medical device and monitor communication systems using infrared (IR), optical, and RF connectivity independent of WiFi. One feature provided by an IR communication system is the ability to positively locate a network resource to a particular room or to determine what side of a wall it is on by use of line of sight optical network communication. What is needed is a medical WiFi adapter that can connect to another medical network to improve location and tracking accuracy over that location accuracy available in WiFi only networks. What is also needed is a medical WiFi adapter that can connect to another medical network to provide a backup route for the transmission of critical care data.

Yet another problem with commercially available WiFi devices is reliability. Generally the communication lines of these devices (including signal, data, and control lines) lack filtering to protect them from radio frequency interference (RFI) or electromagnetic interference (EMI). A static discharge or other interfering signal can cause most WiFi devices to do an uncommanded reset. Therefore there is a need for a medical WiFi adapter that is RFI/EMI hardened.

A related problem with commercial WiFi devices is that these devices can hang or freeze in operation. The only way to clear this fault is to reboot the WiFi device, which usually means rebooting the host processor (usually a laptop or other general purpose computer) as well. It is not practical to reboot most patient care and monitoring devices while they are in patient service. In fact, a medical device reboot could be dangerous or life threatening to the patient in the case of some critical care medical devices. Therefore there is also a need for a medical WiFi adapter that does not freeze, or in the unlikely event of a hang, that can reboot independently of and without rebooting any medical devices for which it is providing wireless connectivity, as well as restore its previous working configuration or alert the host device that a re-configuration is required.

Yet another problem for a commercial WiFi device is to re-establish its network association after a reset. Once reset, a typical WiFi device takes on factory defaults and needs to be re-configured for a given wireless network. While the host can re-configure the card upon reset, it is faster if the card has all the information required to configure itself upon reset. Therefore there is also a need for a medical WiFi adapter that can save its most current operating configuration parameters, reboot as needed, and quickly and automatically re-associate with its intended network.

Yet another problem for commercial WiFi devices involves updating the configuration and firmware within the device. Some commercial WiFi devices can be firmware updated by use of the host computer as by downloading a firmware update from a WiFi device manufacturer and then updating the firmware by executing a small program resident on the host computer over the host computer bus, such as a PCI bus. The problem is that in a typical medical environment the host processor might only be minimally involved in WiFi operation and not able to conveniently accept (as by download) and then update its attached (or otherwise installed) medical WiFi adapter. Moreover, some medical WiFi adapters might not have an available host processor to assist in performing software updates. Medical devices typically lack a interface for configuration and further lack a means of remotely configuring the medical device. Therefore there is also a need for a medical WiFi adapter that can independently receive firmware updates over a WiFi connection without endangering a patient critical care function. Further, there is a need for a medical WiFi adapter that can receive a firmware update for and update the firmware in a host medical device over WiFi without endangering a patient critical care function. What is needed is a medical WiFi adapter that can also provide network applications such as a TFTP, SNMP, or HTTP.

Another problem in medical device applications is that a very large number of medical monitors, instruments, and network-unaware devices can be spread out over a large building or complex of buildings and over many floors of the buildings. Therefore what is needed is a medical WiFi adapter that can take on additional networking roles to facilitate medical WiFi applications in the medical business environment, including bridging between different network types or acting as gateway for a PAN to connect to an IP network, where any additional network functions can be time multiplexed or otherwise time shared if there are any on going or intermittent WiFi client operations, and in a way so as not to jeopardize any critical patient WiFi communications.

Another problem is that commercially available WiFi devices are not well suited to handling input and output (I/O) to or from any port or bus other than the port or bus to which the WiFi device is attached. A small number of specialty WiFi devices have offered additional inputs, such as from a serial communications connection. What is needed is a medical WiFi adapter that can accept (I/O) from a plurality of I/O connections in addition to any host bus to which the WiFi medical adapter might be connected, including one or more serial connections, USB connections, 802.3 Ethernet connections and/or a connection to a parallel interface such as card bus, compact flash, or PCMCIA bus.

What is further needed is a system to support efficient 802.11 communication for different classes of information between the plurality of medical devices and the network. Also needed is a system to prioritize the data so as not to delay time critical diagnostic or monitoring data in presence of non-critical data.

Where a plurality of medical devices is connected to a medical network, the medical network can combine measurements and associate those measurements with an individual patient. The collated measurements can be reported or continuously displayed for a nurse or doctor to view them. The nurse or doctor can form a diagnosis or recognize a critical patient situation that might need short term attention or an emergency response. What is needed is a medical WiFi adapter that can also run one or more diagnostic algorithms accepting input from a plurality of medical devices to take some action such as sounding an alarm to assist a medical professional to quickly identify a patient in medical distress.

There exist a number of United States patents directed to medical device adapters and modules, including U.S. Pat. No. 7,129,836 issued to Lawson et. al. on Oct. 31, 2006. Lawson teaches a wireless patient data acquisition system. Particularly, Lawson teaches an acquisition device that includes inputs to receive data from sensors connected to a patient, a wireless and/or wired transmitter that transmits the data received by the inputs, and a housing. Lawson's device can be further configured to transmit data from a data acquisitions device to a local monitor point-to-point. Lawson does not teach a medical adapter than can be controlled by a host acquisition device, nor does Lawson teach a medical adaptor that converts a non-wireless medical device to a wireless medical device, nor does Lawson teach a medical adapter in a small form such as a PCMCIA, PCI, Compact Flash or 802.11 a/b/g network interface card. Lawson is hereby incorporated by reference in its entirety.

U.S. Pat. No. 6,950,859 issued to Bartek et. al, on Sep. 27, 2005 teaches a method for emulating a physical connection using a wireless connection. Bartek further teaches an adapter with an RF interface, a processor, and a USB interface. Bartek does not teach an adapter capable of transmitting data wirelessly to a network, such as a healthcare provider's wireless infrastructure. Similarly, U.S. Pat. No. 6,850,788 issued to Al-Ali on Feb. 1, 2005 teaches a sensor and monitor interface device, allowing a monitor to wirelessly receive data from a sensor. Like Bartek, however, Al-Ali does not teach an adapter that is capable of transmitting the data to a health care provider's wireless infrastructure. Bartek and Al-Ali are hereby incorporated by reference in their entirety.

U.S. Pat. No. 3,810,102 issued to Parks, III et. al. on May 7, 1974 teaches a method and system for transmitting biomedical data to a remote station for subsequent processing. The system samples and digitizes analog electrical biomedical signals over a communication link. Parks II, however, does not teach a medical adapter that includes a bi-directional wireless radio transceiver. Bi-directional transmission allow for a feedback to inform the transmitter if a re-transmission is required, resulting in a more reliable communication link. It also allows the network to control the instrument and/or the wireless communication link via the wireless communication link. Parks III is hereby incorporated by reference in its entirety.

Therefore, a medical device wireless adapter that is backwards compatible with existing legacy devices and forward compatible with emerging standards, including bi-directional communication is desired.

Further, a medical device wireless adapter that is usable with embedded medical applications and that is also low power, a robust wireless solution with failure recovery, HIPAA compliant, and support for device location is desired.

SUMMARY OF THE INVENTION

The invention comprises, in one form thereof, a medical device wireless adapter ("MDWA") that adapts an existing legacy or newly designed medical data acquisition ("host") device to a healthcare provider's wireless infrastructure.

More particularly, the invention includes a medical device wireless adapter comprising a radio section; one or more means for exchanging data between said adapter and said host device; one or more means for exchanging data between said adapter and a network; a CPU block including integrated support for hosting one or more applications; and one or more memory means; wherein said adapter is configured with one or more host interface modes.

BRIEF DESCRIPTION OF THE DRAWINGS

The present invention is disclosed with reference to the accompanying drawings, wherein.

Corresponding reference characters indicate corresponding parts throughout the several views. The examples set out herein illustrate several embodiments of the invention but should not be construed as limiting the scope of the invention in any manner.

DETAILED DESCRIPTION

Figure 1A:
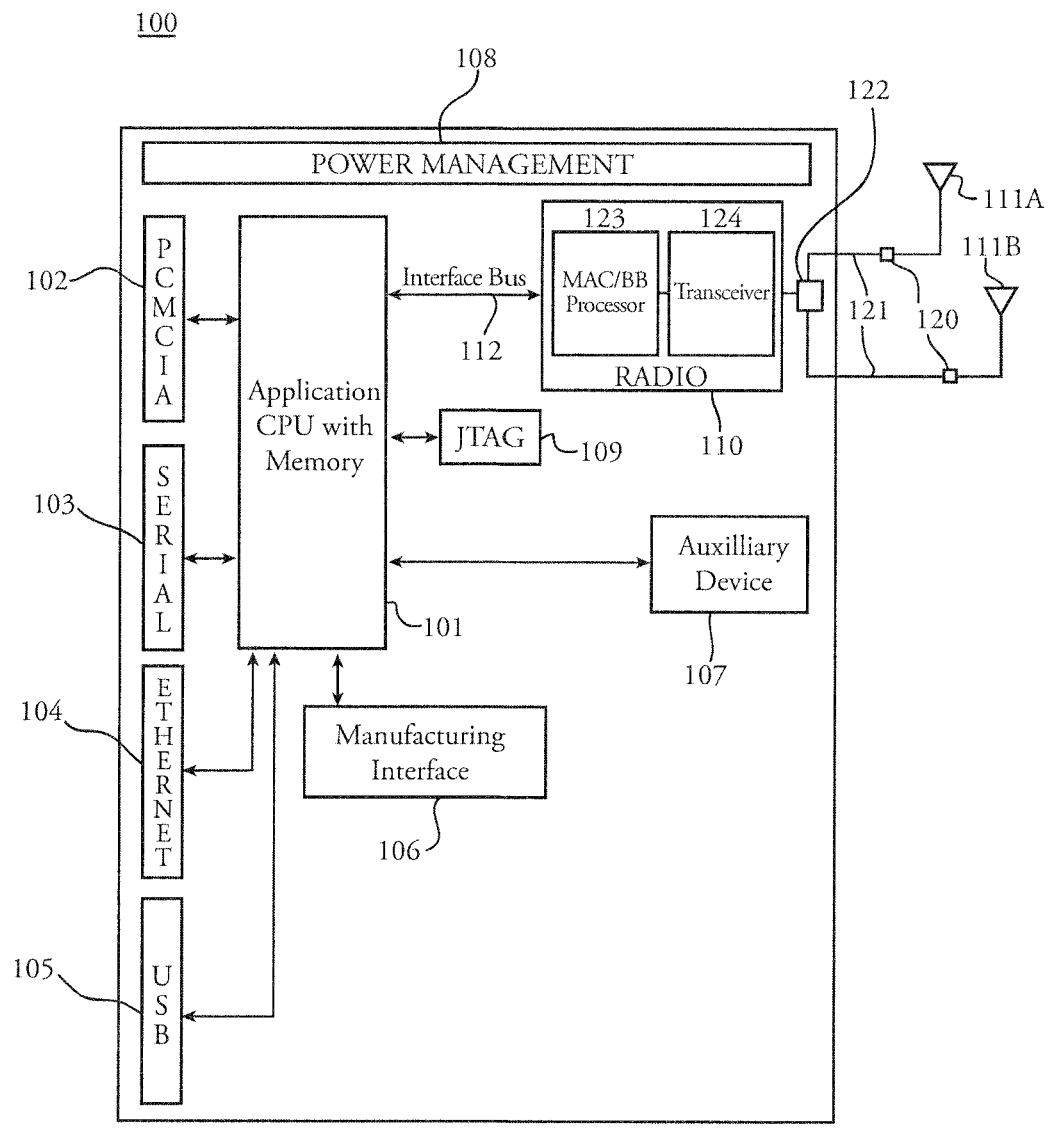
FIG. 1A is a block diagram of a medical device wireless adapter according to the present invention.
Figure 1B:
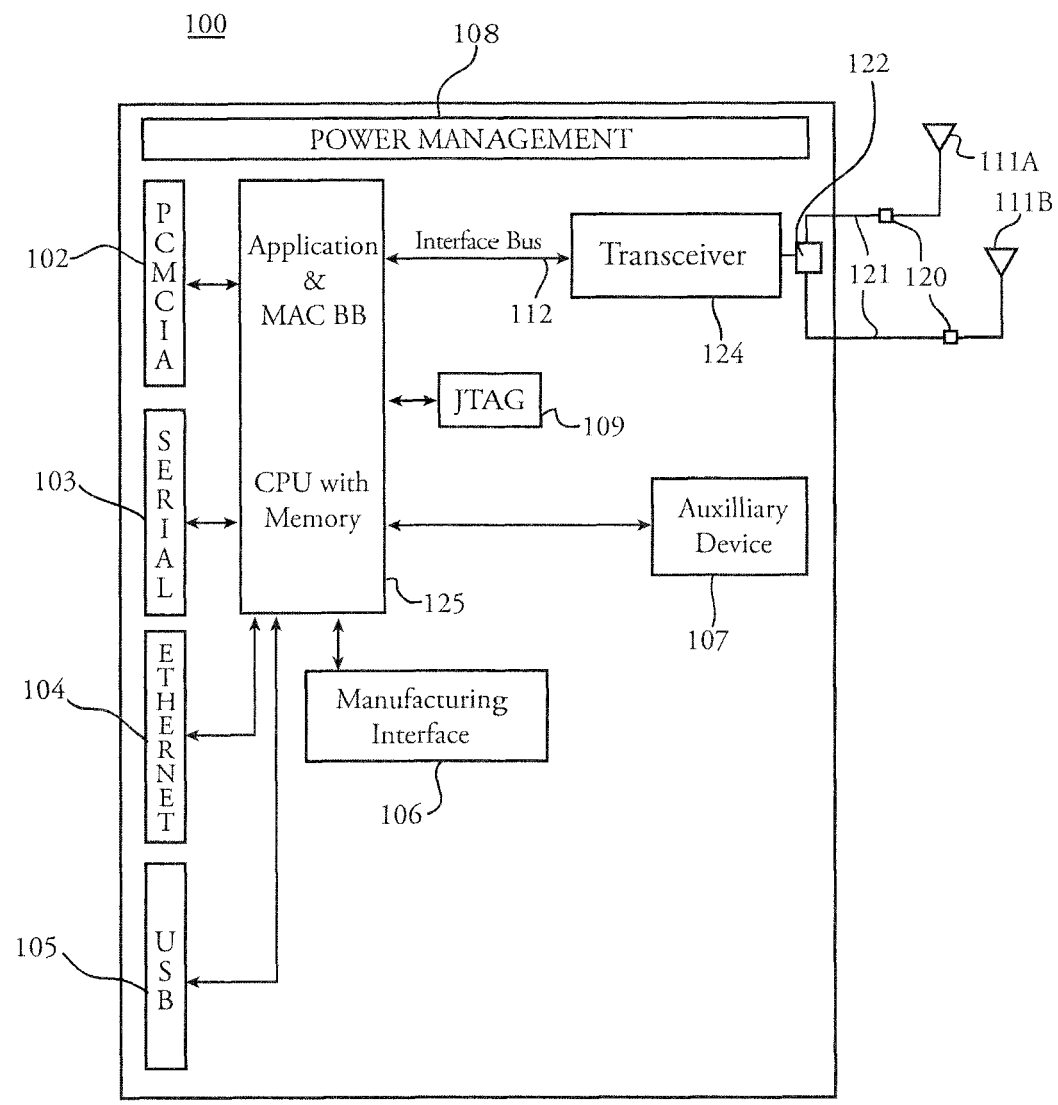
FIG. 1B is a block diagram of a medical device wireless adapter with a single CPU running both the application code and the MAC/BB code.

Referring to FIG. 1A, there is shown a block diagram of a medical device wireless adapter ("MDWA") of the present invention. In one embodiment, the MDWA 100 can connect to and exchange data over a PCMCIA bus 102. This is a particularly convenient way to add wireless connectivity to legacy medical devices having available PCMCIA slots to accept a MDWA 100 in this embodiment, in the form of a PCMCIA card. CPU block 101 (including internal and/or external memory) performs all application computational functions of MDWA 100. MDWA 100 can receive and send data to devices over one or more serial ports 103, Ethernet ports 104, USB ports 105, over the PCMCIA bus, or over other interface known to those skilled in the art, including PCI, CardBus, SPI, IEEE 1394 and I²C. Manufacturing interface 106 can be used to program the Application CPU and associated memory 101 with the MDWA firmware at time of manufacture or in the field via an interface cable (not shown). JTAG block 109 represents self test routines that enhance the manufacturing yield of MDWA 100 by thoroughly exercising many of its functions during power up or by other request for self test, including boundary scan. These test routines can follow guidelines or standards set forth by the Joint Test Action Group (JTAG). The radio section 110 (typically including a MAC-baseband processor 123 and a Radio Frequency (RF) transceiver 124) can comprise a commercially available WiFi RF chip set. FIG. 1B shows an MDWA with the logical function of the application CPU with memory and the MAC/BB processor embodied in a single chip 125. Returning to FIG. 1A, radio section 110 can be further connected to CPU block 101 by the interface bus 112, such as Compact Flash, PCI, SPI, or other bus known to those skilled in the art. Cable 121 and connector 120 can be used to connect an antenna 111A to RF section 110. If optional diversity switch 122 is included, a second antenna, 111B, may be connected, whereupon the MAC/BB processor implements an algorithm to select the best antenna to use via diversity switch 122. Power management block 108 controls and sets the various power modes of MDWA 100. An optional connection to a secondary communication system (auxiliary device) 107 can add backup communication and supplementary location tracking functionality.

MDWA 100 can be a module, board, or plug in device. MDWA 100 can be used to adapt an existing legacy or newly designed medical device (collectively, "Host Devices") to a healthcare provider's 802.11 a/b/g wireless infrastructure. As used herein, "Host Device" refers to any medical device configured to acquire patient data. Alternately, the MDWA 100 can be used to adapt a medical device to a healthcare provider's 802.3 hardwired Ethernet infrastructure. MDWA 100 can provide a number of capabilities, described below, that are not available from any of the commercially available 802.11 a/b/g network interface cards. MDWA 100 can also be suitable for use with Body Area Networks, Personal Area Networks, Wide Area Networks, Metropolitan Area Networks, Cellular networks and other networks known to those skilled in the art. For example, a Serial-to-Bluetooth adapter such as the SMK VRB2211 could be attached to the serial interface 103, allowing MDWA 100 to communicate with a host device over a short-range wireless link as is taught in U.S. patent application Ser. Nos. 10/806,770, 11/031,736, 11/455,368, and 11/455,329, entitled "Personal Status Physiological Monitor System and Architecture," to Welch, et. al., the entire contents of each herein incorporated by reference.

Each MDWA 100 can have a unique MAC address for the Wireless interface, and a unique MAC address for the hardwired Ethernet interface. These addresses can be programmable via manufacturing interface 106. MDWA 100 can also have a Product Serial Number. The serial number can be configured on manufacturing interface 106 and readable via any MDWA 100 interface including interfaces 102, 103, 104, 105, or 106. MDWA 100 can be calibrated digitally and the calibration constants can be read & verified. Note that all functions of the manufacturing interface can be available over any interface, but in the preferred embodiment, manufacturer-specific functions are typically restricted.

Serial port 103 can support RX and TX signals using, for example, bipolar RS-232 signaling levels or TTL-level signals and power can be supplied over the same interface, allowing serial devices to provide power to the radio card analogous to the method used in PCMCIA interfaces. A Power/Serial port 103 can also support handshaking signals such as RTS, CTS, DTR, and DSR signals using either TTL or bipolar RS-232 signaling levels. The RTS/CTS signals can be included for devices that require hardware flow control. The DTR/DSR signals can be included in consideration for a device that asserts a signal to indicate it is ready to communicate and/or support an "On Network" indication, e.g. an LED, on the Host Device without a need for software support by the Host Device. It should be noted that any Power/Serial port input signal can also be used to "wake" MDWA 100 from a low power mode.

In one embodiment, the MDWA 100 operates in complex WiFi implementations, especially including IEEE 802.1x and 802.11i, which support authentication, session key negotiation, certificate management, and encryption down into the MDWA. MDWA 100 can also implement 802.11e quality of service and is upgradeable without support from the host device to support other standards such as improved roaming support (802.11r and 802.11k) as these standards are ratified. MDWA 100 can perform these functions, freeing the Host Device both in terms of compute resources as well as software complexity. Note that use of a commercial off the shelf wireless card would push much of this implementation into the device driver, or DLL, and as a result onto the host processor. While such a sharing of computational resources can be acceptable where the host is a Windows laptop with a 1-2 GHz processor and no real-time constraints, it is not a desirable solution for a host medical instrument, such as a Vital Signs Monitor.

By way of example, there are at least two methods in which the MDWA can be used to interface with a Host Device. The first method comprises a Host API Mode, in which the Host Device integrates a small set of code known as the Host Applications Programming Interface (API), or Host API Proxy, which allows the Host Device to manage and control the MDWA through an applications interface. The second method utilizes an Adapter Mode, in which the Host Device does not integrate any code, and operates in the manner it was originally designed, e.g. simply transmits raw data on a serial port. In this mode, the MDWA can detect that a device is ready to establish communications with a serial device, e.g. term server, and adapt that protocol to allow the device to establish communications. The MDWA does this by monitoring the data and/or control lines of the appropriate interface, and then acts on behalf of the device to present said device to the network. Once device communications has been established and completed, as by a proprietary rendezvous or similar discovery protocol, the MDWA becomes a simple pass through device, forwarding packets between two interfaces. The rendezvous protocol is described in greater detail in co-pending and commonly owned U.S. Pat. No. 6,616,606, "Patient Monitoring System," the entire contents of which are incorporated herein by reference. Data traffic and/or control line status can also be used in this mode to detect that a connection should be timed out, and the process restarted.

Host API Mode

In one embodiment, the MDWA provides a single, common Host Application Program Interface (API) regardless of which interface is used by a given Host Device (Serial Port, PCMCIA, USB, or other alternatives). Complete functionality can be provided over all of the available interfaces. This common API encourages reuse of software components across multiple product lines, further reducing the effort to integrate the MDWA with subsequent devices.

In one embodiment, the Host API Proxy can be a small set of code that is ported to each host device, which is responsible for packaging commands and data to be multiplexed with other network data traffic, and sent to or received from the MDWA over the appropriate interface. Unlike modems and some prior art devices, which share a single channel for network data and control information, this proxy can communicate over a set of distinct logical channels that coexist concurrently with the control channel used to manage the MDWA.

The code can also encapsulate the process of creating packets to be multiplexed over the appropriate interface (RS-232, PCMCIA, Ethernet, USB, or other interface), destined for either the command interpreter or a specific socket endpoint. In one embodiment, the MDWA provides deterministic behavior with respect to command traffic and data traffic that is multiplexed onto the serial port or other interface. Note that some serial interface devices, such as modems, transition a single serial connection between command mode and data mode when a connection or attachment is made with the other end of the network. While an escape sequence or control signal marks these transitions, in many cases it is impossible for the host device to tell whether the serial port was in command mode or data mode at the instant the last command or data packet was sent. The MDWA software is adapted to address this problem through the use of a multiplexing layer, which can identify and route to several logical destinations, independent of the state of the other destinations. The use of a multiplexing layer enables multiple network endpoints to be active at the same time, regardless of the type of interface. Some medical device protocols require that two distinct ports be open at the same time, e.g., one for the rendezvous packets, and one for instrument data packets. As a result, the Host Device needs to be able to send and receive data for at least two different ports, plus commands for the MDWA over a common channel. This channel can be any available host interface, e.g., USB, Ethernet, Serial, PCMCIA, CardBus, Mini-PCI, and others generally known to those skilled in the art.

For example, when using interfaces such as PCMCIA and Ethernet, one could simply assign these functions to different port addresses. In one embodiment, the MDWA is adapted to send/receive data to/from multiple endpoints over a common channel, allowing fully capable wireless adapter functionality over less capable interfaces such as RS-232. The Host API Proxy provides a proxy for network communications using an object oriented C++ API styled after BSD Sockets. Examples of this can be found in the Java and C #socket APIs.

Adapter Mode

Adapter Mode provides the wireless adapter the ability to adapt so-called "dumb" host devices, such as a legacy Infusion Pump or other network-unaware devices. These adapted devices can then communicate with at least one central monitoring station, at least one server, or other controlling system product, and enable management and tracking of those devices by the IT network staff.

In this context, the Host Device does not integrate the Host API Proxy. Rather, the MDWA actively presents the Host Device to the network. The MDWA is further adapted to execute rendezvous or discovery medical protocols on behalf of the attached Host Device. In this embodiment, the protocol can comprise a UDP packet of a pre-defined format that is broadcast to the network on a well known port. This broadcast packet can include a unique device identifier that is a requirement for networked system products, even where the legacy device does not provide this capability. The unique identifier may be configured into the MDWA, either during provisioning or during customer configuration on site through a web or command line interface.

Once the initial rendezvous or discovery process is complete, the MDWA passes bidirectional data between the device and the networked system. This enables even a network-unaware device with only an RS-232 serial port or USB port and no network stack or other supplemental software to become a "Full Network Citizen," with minimal or no modification to the existing device.

In this embodiment, the MDWA also automatically enables a network connection by completing the steps of association, obtaining an IP address, and authenticating. Furthermore, an application on the MDWA may provide the bridging of the communications data between the native device and the TCP/IP network interfaces.

In another embodiment, the MDWA communicates with the Network Host with either a real-time rendezvous or a store and forward mechanism, such as e-mail or pager notification. For real-time rendezvous, a pre-defined packet is transmitted as either a broadcast or directed packet to a server in order to establish a link between the host device and the server. In the case of store and forward, the MDWA buffers the information until it can be handed off to the destination, such as an e-mail or paging service. Initiation of either of these communication methods can occur upon assertion of a control line, or upon receipt of a packet the host normally sends to communicate with another RS-232 device. In a further embodiment, the MDWA Power Modes, including Hibernate, can be automatically controlled by the application running on the MDWA, based on traffic analysis. MDWA Power Modes are discussed in more detail herein.

In one embodiment, the manufacturing interface 106 supports manufacturing configuration of the call method. This defines the initial control signal behavior, or the initial bytes that would be transmitted/received by the MDWA to begin communications with the Host Device.

Figure 2:
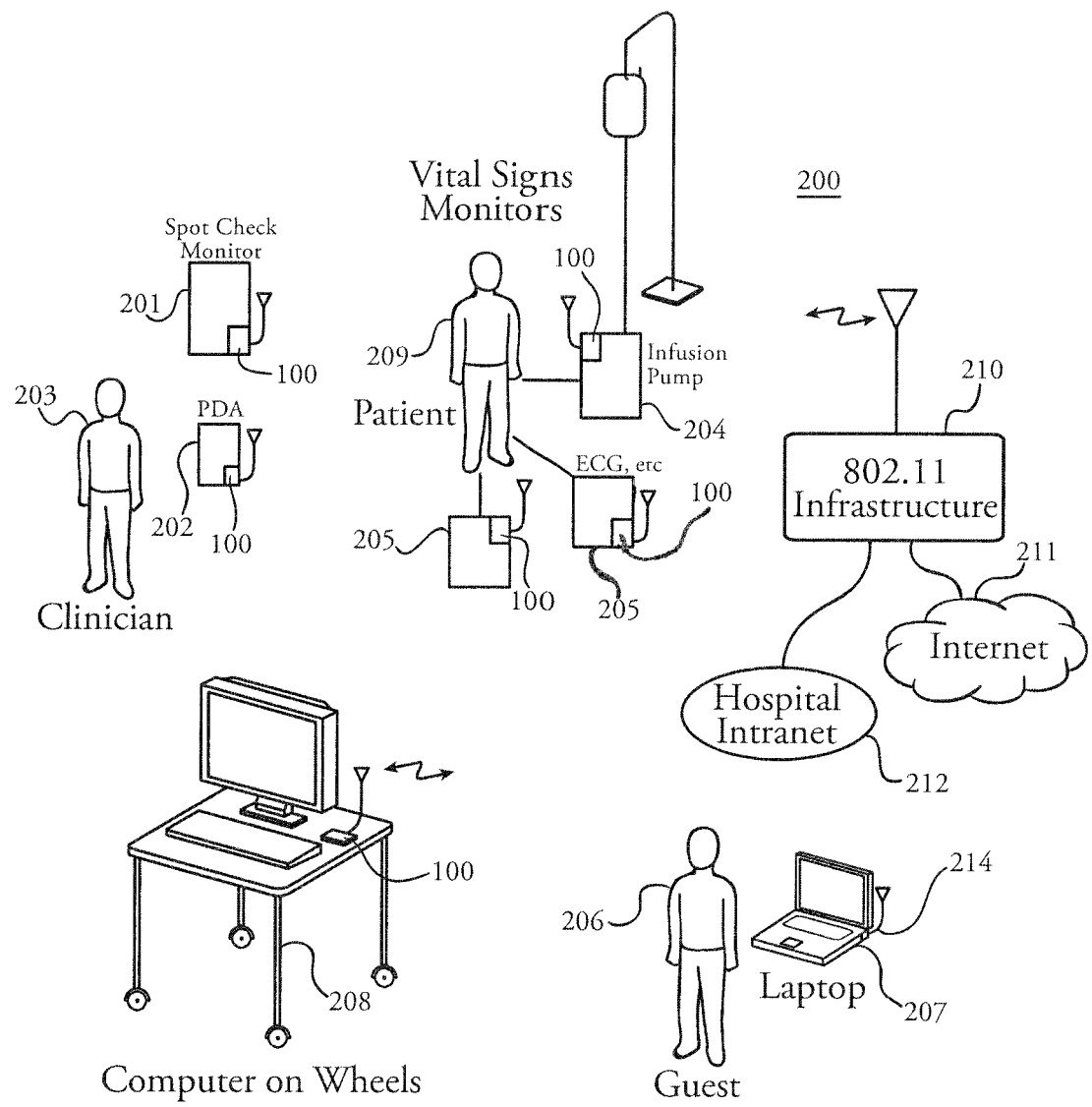
FIG. 2 shows a block diagram of an exemplary medical network infrastructure.

An MDWA 100 as so far described can be used as a part of the Wireless Infrastructure of a hospital or clinical office. FIG. 2 shows a block diagram of an exemplary medical network infrastructure 200.

The MDWA is configurable to address several different classes of Host Devices. The most "mission critical" of these devices are those that must communicate adverse patient conditions, such as patient alarms from continuous vital signs monitors 205, and equipment alerts from infusion pumps 204. Monitors 205 are typically attached to a single patient 209 for hours or even days, and report alarms in addition to capturing various physiological variable data including, but not limited to, pulse rate, and body temperature, as well as ECG, pulse oximetry, and additionally periodic measurements of blood pressure as needed. Vital signs monitors typically include sensors or other electrodes for acquiring patient data. The MDWA is also configurable to address body worn sensors. An example of this type of host device is more specifically described in co-pending U.S. patent application Ser. No. 11/591,619 entitled "Body Worn Physiological Sensor Device Having a Disposable Electrode Module," to Baker, et. al., filed Nov. 1, 2006, the entire contents of which are incorporated herein by reference. In addition to monitors, several other types of devices can co-exist on a network. These include devices more fully described herein.

Spot Check Monitors 201 are devices that can typically travel with a Nurse or Clinician 203, and are used to acquire and upload individual readings while the clinician is present with a patient 209. Wireless connections in these devices allows the patient data to be transacted directly to the Clinical Information System (CIS) or Hospital Information System (HIS), via an interface such as HL7, which interface is implemented on the MDWA.

Infusion Pumps 204 are devices that can use a wireless network to download Drug Libraries and Medication Rules, avoiding the need for a bio-technician to track down and interact with each and every pump in the hospital. Downloading Drug Libraries and Medication Rules is aided by the MDWA that buffers the Libraries and Rules analogous to how it buffers new firmware for the host device, as is taught later in the specification In addition, prescriptions can be transferred over the wireless infrastructure to an infusion pump so that a clinician need only confirm the order or the clinician input can be transferred over the wireless infrastructure to the pharmacy and verified against the original prescription order. While wireless infusion pumps exist, they do not implement strong authentication/encryption and a bevy of legacy infusion pumps are in use in hospitals today.

Personal Digital Assistants 202 are handheld devices that can be used by a clinician to record and/or receive clinical information, including physiological alarms, and interact with other systems in the hospital.

Mobile diagnostic workstations or Computer on Wheels (COWs) 208 are PCs that can be used for clinical activities such as vital signs charting, CIS access, HIS access, and/or the ordering and accessing of Clinical Lab results such as by a hospital intranet 212. One specific application is described in U.S. patent application Ser. No. 11/131,015, "Mobile Medical Workstation," filed May 17, 2005, the entire contents of which are incorporated herein by reference.

Network Access to the hospital intranet 212 can be provided by a connection to a medical 802.11 wireless infrastructure 210 by MDWA 100 and by other hospital devices. Guest network access is a capability that allows patients and visitors 206 to use laptops 207 with wireless capability, such as a commercial general purpose 802.11 adapter 214, to access the Internet 211 while they are in the hospital.

For medical devices and instruments that provide Continuous Vital Signs Monitoring, there is an increased expectation of system reliability, including the need for a high reliability 802.11 medical network connection. By contrast, at a slightly less demanding level of reliability, Spot Check devices can use whatever network is available (including wireless infrastructure 210), whether or not it meets the mission critical requirements.

Figure 4:
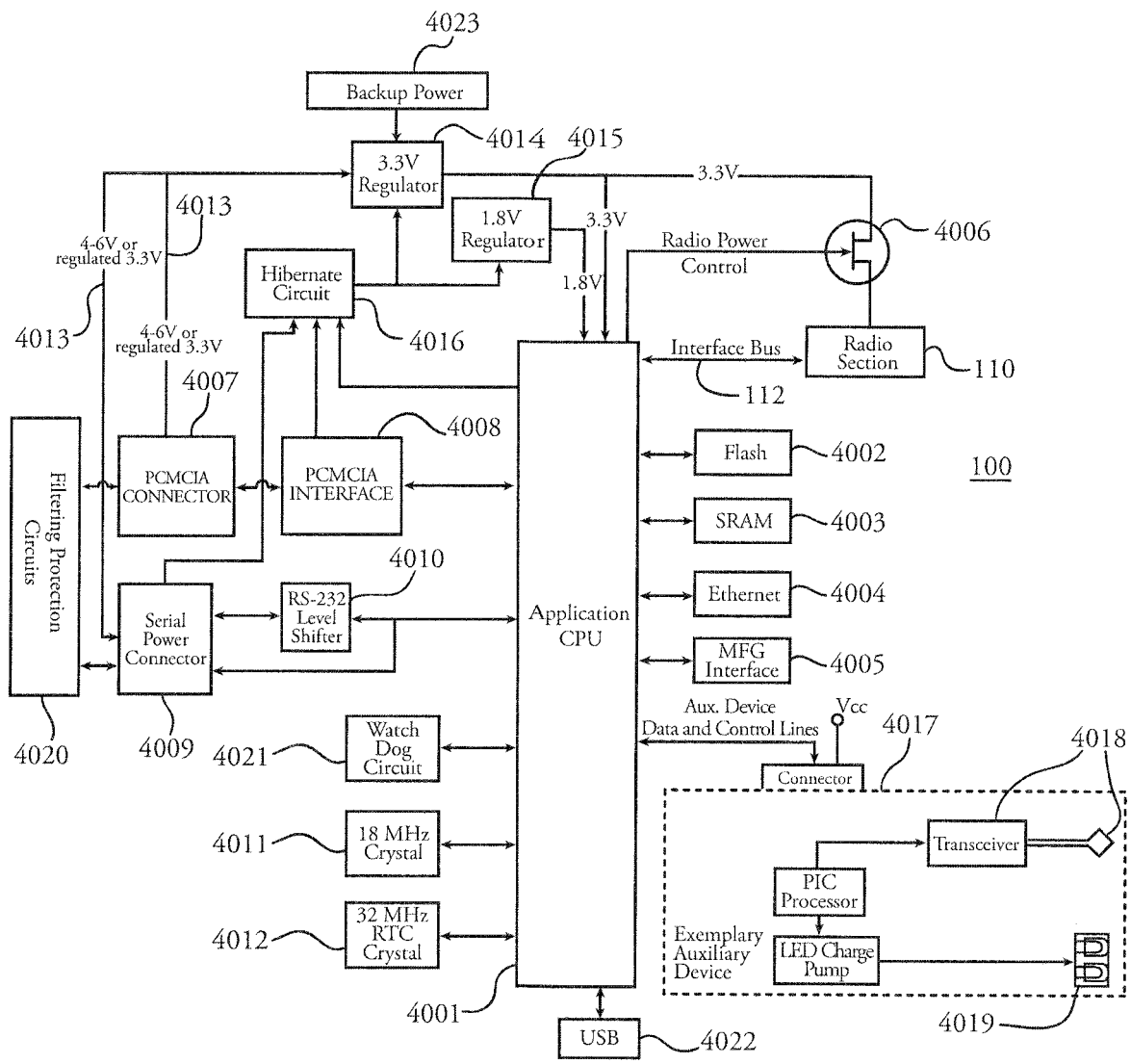
FIG. 4 shows a block diagram of an exemplary MDWA in greater detail.

FIG. 4 shows a more detailed block diagram of exemplary MDWA hardware according to the invention that has been found useful to test the various functions of a MDWA as described herein. The CPU and some memory function of 101 in FIG. 1 were provided by an AT91RM9200 4001 manufactured by the Atmel Corporation. The AT91RM9200 includes a 200 MIPS ARM920T processor with 16K-byte instruction and 16K-byte data cache memories, 16K bytes of SRAM, 128K bytes of ROM, External Bus Interface featuring SDRAM, Burst Flash and Static Memory Controllers, USB Device and Host Interfaces, Ethernet 10/100 BaseT MAC, Power Management Controller, Real Time Clock, System Timer, Synchronous Serial Controller, 6-channel Timer-Counter, 4-channel USART, Two-Wire Interface, Serial Peripheral Interface, Multimedia Card Interface and Parallel I/O Controller. The AT91 supports slow clock and idle modes that are used to support low-power operations discussed below. Additional memory as represented by block 101 of FIG. 1 was present as FLASH memory 4002 and SRAM memory 4003. Debugging was accomplished with the use of an Ethernet Debug connection 4004 (connector not shown) and Serial Debug connection 4005 (connector not shown). A radio section 110, comprised of a Conexant MAC/Baseband processor and transceiver (Voyager chipset) coupled to AT91RM9200 4001 via a CompactFlash Interface Bus 112. The power to radio 110 is controlled by FET 4006, to support low-power modes discussed below. The PCMCIA interface 102 of FIG. 1 was provided by PCMCIA connector 4007 and PCMCIA circuit interface by a Universal Asynchronous Receiver Transceiver (UART) 4008. The USB port interface 105 of FIG. 1 was provided by USB connector 4022. Although not implemented in the example, it is contemplated that any connector that would connect to the host, including USB connector 4022 and Ethernet Debug connection 4004 can also be coupled to hibernate circuit 4016, preferably coupled via Filtering/Protection circuits 4020. A decision to couple an interface to the hibernate circuit depends on the power used by that interface. In the present embodiment, only serial and PCMCIA physical host device interfaces are supported, therefore Ethernet and USB are disabled to save power. The serial port interface 103 of FIG. 1 was provided by serial/power connector 4009 and RS-232 level shifter 4010, allowing either TTL or RS-232 level signaling. Timing and clocks for the AT91RM9200 4001 were supplied by 18 MHz crystal 4011 (CPU clock) and a 32 kHz RTC (real time clock) Crystal 4012. MDWA power supplied by a 3.3V regulated or 4 V to 6 V unregulated power source 4013 and regulated by a 3.3 V regulator 4014 (if required) and a 1.8 V regulator 4015. Note the topology of the regulatory circuits depends is optimized for best efficiency and in some designs, the lower voltage regulator may run directly off the input power source. Hibernate circuit 4016 provided part of the power mode control system. Filtering/Protection Circuits block 4020 comprises a filter to remove RFI/EMI signals that could cause an uncommanded reset of application CPU 4001. It should be noted that any communications (signal) line can also be advantageously filtered, including reset, data, and other signal lines. Watch dog circuit 4021 provides an external monitoring circuit to detect and restart the module in the event of a software application failure or operating system fault. An auxiliary device such as a location hardware block such as is manufactured by Radianse, Inc. of Lawrence, Mass. 4017 is supported to supplement MDWA functionality. For example, optical communications block 4019 can aid in locating an asset using the MDWA to tell for example, what side of a wall the asset is on (while RF energy from Radio 110 and RF block 4018 can penetrate a wall, the light from optical communications block 4019 cannot penetrate an opaque wall). Further RF block 4018 can provide backup data communications to the MDWA 802.11 network connection. It should be noted that other public domain and proprietary hospital communication networks and channels can be added to an MDWA in addition to, or in place of the Location/communication 4017 function, or the MDWA can operate with no supplementary location/communication system.

Figure 5:
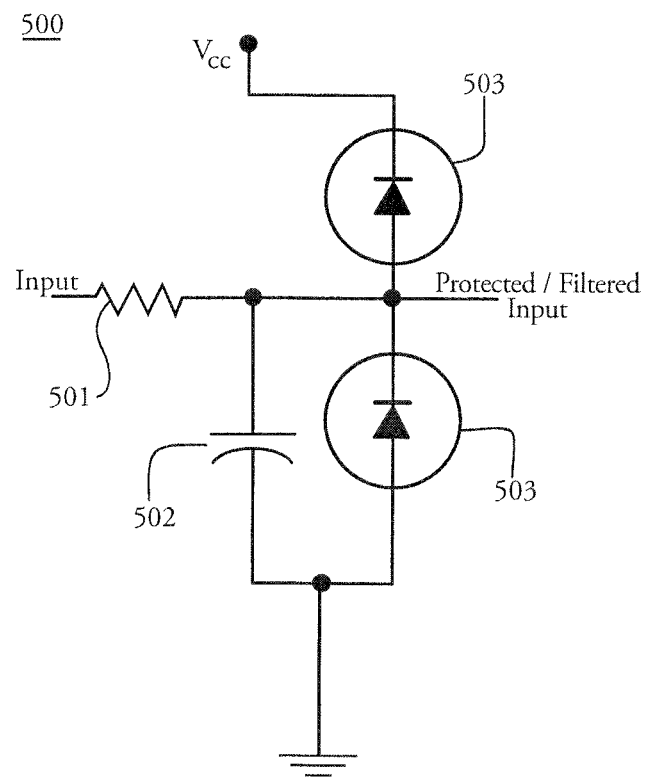
FIG. 5 shows an exemplary communication line filter.

Referring now to FIG. 5, filtering of data, signal, and control lines, such as a reset line, can be achieved using a low-pass filter, such as implemented by the RC section (R 501, C 502) of the circuit 500. In addition, if ESD protection is required, diodes 503 to supply and grounds may be used. Depending on data speeds and immunity levels required, the capacitance of diodes 503 can serve to provide enough low-pass filtering to provide protection against signal glitches from external sources.

The MDWA of the present invention typically supports IEEE standards including 802.11a, 802.11b, and 802.11g PHYs, but can be extended through firmware update to support 802.11n. To that end, a TCP/IP stack can comprise a minimum of four layers, including full support for UDP, TCP, ARP, DHCP, and ICMP. In addition, applications are included to provide support for TFTP and web-based services. This MDWA can further provide support for a rendezvous protocol, e.g., a predefined UDP broadcast packet. Also, client support can be provided for DNS, NTP, SNMP, and other network protocols known to those skilled in the art.

The following is a summary of MDWA 100 wireless adapter functions that can be performed in firmware running on CPU block 101. We note that Radio Section 110 includes a CPU and all aspects of Radio CPU can run on the Application CPU 4001 and vice-versa. In a preferred embodiment, a single CPU in on the radio card implements MAC/Baseband and applications functions.

Asset Tracking

An Asset Tracking and Real Time Location Service (RTLS) using MDWA 100 can be done in at least two alternative technologies. The first is based on a hybrid IR/RF capability that can be provided by a secondary communication system attached as exemplary auxiliary device 4017 and the second is based on 802.11 Access Points receiving and examining the signal strength and/or latency of 802.11 packets. Note that some asset tracking solutions support a minimal communication channel. An exemplary back-up communications system could be set up using an AeroScout, Radianse, or PanGO module combined with an 802.11 infrastructure. An 802.11 client can be tracked by the infrastructure to which it connects, as illustrated by thin AP solutions from Aruba Wireless Networks and Cisco Networks, however, when that client goes off the air, tracking ability is typically lost. Dedicated 802.11-based tracking tags such as those offered by AeroScout or PanGO last for years, but work only on 802.11b/g infrastructures and do not support full 802.11 client communication. The MDWA can also provide uninterrupted tracking operation, where the Asset Tracking function is provided even for periods when the Host Device power has been turned off, or the main battery has been removed. The MDWA provides an auxiliary power input where a backup power source 4023 provides sufficient energy for the MDWA to beacon as if it were only an asset tracking tag. That is, the MDWA can be placed in a low-power state where it is programmed to provide asset tracking functions. Upon exit from this state, full 802.11 radio functions are restored. Tracking can continue based either only on 802.11 data traffic, or 802.11 data traffic and transmissions specifically tailored for tracking, such as transmitting on every channel periodically to ensure that all nearby APs contribute to the position determination. To save power, the MDWA (or a simple asset tracking tag) can occasionally determine which APs are nearby (e.g. using 802.11r or probe requests) and only transmit on those channels. Asset tracking can be used to track assets, patients, and personnel. Asset tracking makes it possible to find equipment and decreases the time it takes to find wheelchairs, infusion pumps and other equipment. This enables the hospital to better manage their medical equipment assets. An alarm can sound if equipment is removed from its approved area. Patient tracking allows a patient to be found quickly in the event that the patient has an event and also allows the hospital to manage patient flow to decrease wait time. Personnel tracking allows the hospital to send the nearest clinician when a patient is in trouble and allows the hospital to manage workflows so that clinicians arrive when needed, e.g., alert a surgeon so that the surgeon does not arrive before the surgical suite is ready, or before the patient has been prepped.

Converting to an Asset Tag

Any active 802.11 radio can be located by infrastructures such as those available from Cisco Systems and Aruba Networks. Similarly, asset tags can be located through its periodic beacon, though these devices cannot maintain a network connection. When an 802.11 radio is inactive, locating it becomes impossible unless it takes on the character of an asset tag, transmitting an occasional location beacon. This location beacon could be implemented by occasionally awakening and establishing a network connection or it could include full emulation of an asset tag, including beaconing that allows location detection without a full network connection (saving power compared with establishing a network connection). Modifying the number of beacons per unit time can be modified to trade off battery life for how often the location is updated, a feature that exists in asset tags, but not in radio cards. In addition, when the MDWA changes to asset tag mode, it can modify the transmission power to trade off location accuracy with battery life (generally, the more APs that hear the device, the smaller the location error). The MDWA may move into asset tag mode when either primary power is removed from the MDWA or the MDWA is placed into one of the low-power modes. To save power, the MDWA may use a different Operating System when operating in beacon mode. When the MDWA has data to transact, it automatically leaves low-power mode and the asset tag mode and enters full 802.11 radio mode to support data transmission.

Adding Location to the Patient Context

Patient mobility is a well-known contributing factor to faster recovery times and wireless monitoring of patients has existed for many years, augmenting hard-wired (typically with more parameters) bed-side monitors, to provide for patient ambulation. When hard-wired patients need assistance, it is simple to determine their location. Some bedside monitors can run in wireless mode as the patient is transported and some portable monitors support multiple parameters, allowing their use on more acute patients. What is missing is the risk mitigation for the use case of when the ambulatory patient needs assistance and needs to be found— that is, adding location to the patient context. Patient context is defined as the set of linked data that identify a patient or pertain to a patient. Items such as name, patient ID, current state of physiological parameters, alarm limits, the Monitor ID and location together provide the patient context.

For location to be added to the patient context via the location of the patient monitor, one must ensure that the monitor is not inadvertently switched to another patient.

Once a clinician attached to a patient and configured with alarm settings and the patient name, the monitor can detect when it loses physical connection with the patient because physiological inputs disappear. As long as the monitoring is continuous, one can be sure that the patient is the same. While another networked device can perform this function, when the network connection is temporarily lost, only the patient's own monitor can ensure that the monitoring has continued uninterrupted.

When the patient context includes location, the patient can be located in the event he needs to be found, which could be due to various reasons including a fall, loss of communication, patient pressing the nurse-call button, or physiological alarm. Patient context can be built using a location tag that is separate from the patient monitor, but then the link of asset tag to patient must be made manually.

Implementing the location feature requires that a binding between the location tag and the remaining components of the patient context is made. As mentioned above, this binding can be done automatically and accurately when the location tag is permanently affixed to or part of the patient monitor.

The location solution is typically comprised of a location engine, location sensors (APs in the case of 802.11-based location), and the location or asset tags. Location sensors are mapped onto the coordinate system of the location engine and the location of asset tags is mapped to this same coordinate system. The location engine populates a database, consisting of at least X,Y coordinates and the identifier for the asset tag. Often, additional information including time and height and meta information such as the asset type is included in the database.

When a patient monitor indicates the patient to whom it is bound needs assistance, the monitoring server queries the database (either by shared access or an API to the location engine) for the location of the bound asset tag. The coordinates are translated, as necessary to map from the location server's coordinate system to the monitoring server's coordinate system. The monitoring server can then provide audio, text, and or graphical indications that the patient is in need of assistance and where the patient is located. These indicators could occur on a PC, a PDA, cellular phone, hallway message panel, or other signaling device. For example, a map of the hospital could indicate a flashing red heart at the location of the patient, the patient waveform window can indicate "Arrhythmia, Room 214," and an audio circuit could annunciate, "Arrhythmia, Room 214".

Additionally, annunciators can be activated when a clinician needs to find a patient, as when it is time for a lab. Graphic annunciators can be active at all times, or only activated upon an event occurring.

Power Modes

Figure 3:
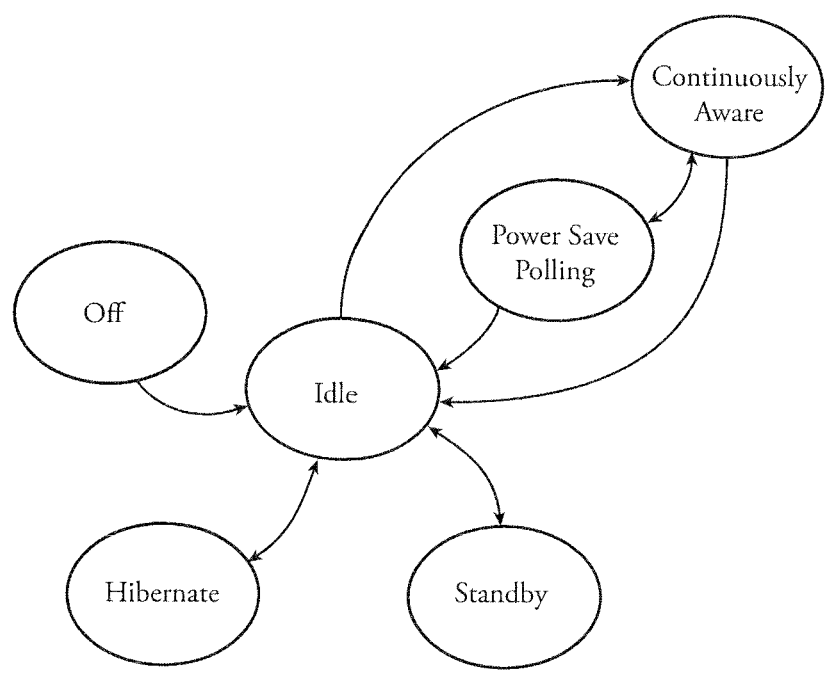
FIG. 3 is a power mode state transition diagram for an exemplary MDWA.

Support for multiple power modes can address the differing needs of medical devices in the healthcare environment. This includes use models for Continuous Vital Signs monitoring, Spot Check monitoring, and other clinical devices in need of network connectivity, such as Infusion Pumps. These power modes can provide a seamless transition on and off the network in support of lower power operation or stand alone operation, and are fully integrated with the Asset Tracking and Location Service capabilities provided by the MDWA. The preferred embodiment of the MDWA supports a selection of at least five distinct Power Consumption Modes when power is applied to the card. In addition, a sixth state of Primary Power Off (no power applied to the main power connector) provides a limited functionality of the Location Service through the backup power source 4023. The MDWA power modes are shown in the power mode state transition diagram of FIG. 3.

When first powered up, the MDWA transitions to Idle mode once initialization is complete. Unlike traditional cards, this allows the device to be placed in a low power state, remain there as long as needed, and be ready to transmit a radio packet in a fraction of a second after the command is given to transition to an active mode. Existing radio cards drop association when changing power modes, resulting in a loss of network connection. In contrast, the MDWA is capable of transitioning between the first two modes, Continuously Aware and Power Save Polling (PSP), by API control without loss of association with an Access Point. Further, the PSP sub-mode can be changed by API control without loss of association. The MDWA is able to transition between the two active transmission modes (Continuously Aware and Power Save Polling) and Idle mode by API control. The MDWA is also able to transition from any of these first three modes to Standby or Hibernate mode by API control, and it can further transition from Standby or Hibernate mode to Idle mode by toggling one of the control or data lines on the active host interface (e.g., PCMCIA, or Serial Port, or USB interface). This transition based on external input allows the MDWA to stay in Hibernate or Standby mode for extended periods with out activating the CPU, thereby saving energy.

In the preferred embodiment, in the Continuously Aware Mode, the transceiver is either continuously on, or wakes up at least once per beacon interval in addition to waking to transmit data as soon as it is received from the host. This mode is typically used for short periods of time when the Network Host or Host Device have large amounts of data to transfer and/or many commands to process. The Location capabilities can be fully operational in this mode, with either high or low resolution. Lower resolution saves power by either transmitting at an increased interval, lower power level, or using only one of the physical interfaces, e.g. RF and not IR.

The Power Save Polling Mode of a preferred embodiment allows the Host to control a requested PSP mode (PSP-n) over the Host Interface. For example, in PSP-10 mode, the MDWA awakens every ten intervals, approximately once per second. The transceiver could awaken to transmit data received from the host immediately upon receipt of the data, but to save power preferentially synchronizes the data transmission with an already scheduled beacon awakening. This function is either built directly into the MAC layer, which buffers data until a beacon occurs, or the host waits until it is notified that the radio is awakened and then immediately pushes the data to be transmitted to the radio. The Location capabilities can be fully operational in this mode, with either high or low resolution.

In a preferred embodiment including an Idle Mode, the MDWA's CPU can be ready with the radio is turned off. In this mode, the Host Device is able to issue commands, change configuration parameters, and receive status over the Host Interface. The Location capabilities can be fully operational in this mode, with either high or low resolution. The capability of booting to Idle mode enables the boot process of the MDWA to take place in parallel with the boot process of the Host Device. Once started, the Host Device can place the card in any of the alternative modes. Alternately, the MDWA can boot to any power mode.

A Standby mode is intended to support applications with a use model indicating intermittent network connection. Here, wireless connectivity can be turned off until it is time to upload a dataset, and this mode supports a faster time to establish a network connection as compared to the Hibernate mode. In the preferred embodiment of the Standby mode, the CPU will be "asleep" and the radio will be turned off. The CPU will "wake up" upon the reception of Host API Proxy data on one of the host interfaces. The last known AP and channel are retained, precluding in many events the need to search for an appropriate AP. The Location capabilities are fully operational in this mode, with either high or low resolution.

The Hibernate mode supports applications where the radio has been disabled for a relatively long time, but still can benefit from a fast network connection time. This mode uses almost no power and allows the host to effectively turn off the radio, while providing a faster network association time than is possible when leaving Power Off Mode. In a preferred embodiment, the CPU and the radio are turned off and the last known AP and channel are retained. The Location capabilities may be fully operational in this mode, with either high or low resolution. Because of the extremely small power consumption in the Hibernate mode, instruments make use of the Hibernate mode in multiple situations, including when the user-accessible soft power switch is "turned off," and when the instrument needs to operate in a reduced functionality mode due to depletion of the battery. A low-power hibernate circuit 4016 re-powers the Application CPU 4001 to exit hibernate mode.

In one embodiment, the MDWA includes an internal latch in order to keep track of whether the Power-On Self Test (POST) has completed successfully. Once the POST has completed (i.e., due to a power-on reset), it is skipped on subsequent transitions out of Hibernate mode.

In a further embodiment, a backup power input 4023 can provide power for a Real Time Location Module when no power is applied to the main power input (Power Off Mode). In a preferred embodiment, the loss of power from the main supply causes the Location Module to transition to a lower power mode.

Persistent Data

The MDWA can also store persistent data across power off/on cycles and rebooting such as its authentication state, which radio band is in use, e.g., 802.11a or 802.11g, ESSID, power mode, IP address, MAC address, calibration factors, and current AP, regardless of the selected power mode. Storing these data allows the MDWA to reboot and initialize faster than depending on an external source to provide the data. It also provides a method to often avoid the time lost to scan channels to find an available AP.

Changing Power Modes

While a typical application running on a PC shows no ill effect due to the radio card resetting when the radio card operation mode is changed, alarm data and streaming data may be lost during an MDWA reset. To avoid losing data in these events, in power modes where the CPU is awake, the MDWA can apply configuration changes dynamically without a reset.

Network Protocol Delegation

All network protocols required for communication, authentication, and network management can be encapsulated by the MDWA. A full TCP/IP Stack is also provided by the MDWA, and is exposed to the Host Device through a Host API Proxy for Host API Mode, and through a bridge application for the Adapter Mode. A proxied TCP/IP stack on the WMDA avoids the need for a TCP/IP stack on the Host Device, in order to communicate with wireless or wired Ethernet, further reducing the complexity and resource requirements imposed upon the Host Device.

The MDWA can include Port Based Authentication (802.1x), Wireless Encryption (802.11i/AES and WPA/TKIP), Quality of Service (802.11e), DHCP, NTP, SNMP, and other network protocols familiar to those skilled in the art. We note that the MDWA can be upgradeable to support new networking standards and protocols as they are developed. Note that these delegations are useful for any embedded host, not simply a medical device.

Bi-Directional Authentication

One embodiment of the present invention includes bi-directional authentication of the Host Device and the healthcare infrastructure using Certificates, which protects both the device and the infrastructure from adversaries. Certificate Management and Processing can be completely encapsulated by the MDWA. In one embodiment, there can be provided a minimum of two certificates: "OEM" and "Customer". The 802.1x authentication protocol supports this functionality for both wireless and hardwired Ethernet, allowing a single authentication mechanism to be used with either of these external interfaces.

An OEM certificate can provide "Out of Box" device operation with system products that have the matching server-side certificate, such as an Acuity Central Monitoring Station available from Welch Allyn, Inc., connection server, or other device based on a trust relationship established with the medical device manufacturer. The Customer certificate enables those customers that wish to manage their own certificate hierarchy to do so, without disturbing the OEM certificate that can still be used to enable service support and software updates.

Multiple authentication types and certificates can be supported by the MDWA. The MDWA has a selection algorithm that can present the most likely certificate to be accepted based on past history or a configuration setting. If the most likely certificate is rejected, the algorithm can then present a second-most likely certificate, and so on. In many clinical contexts internet access is not available, thus with the device the full certificate chain for the server is installed, supporting bi-directional authentication, independent of external resources. A MDWA can provide a full interface to manage certificates and passwords.

Overview of Digital Certificates

Digital Certificates are the foundation of secure authentication for 802.11 a/b/g Medical Devices and Infrastructures. Certificates provide a means of bidirectional authentication that is vastly more secure than commonly used "secrets" such as usernames and passwords, while at the same time avoiding the need for a clinician to enter any information at the medical device.

A digital certificate binds the identity of a person or device (the Distinguished Name) with a Public Key. This enables bidirectional authentication, which protects both the infrastructure from rogue devices, as well as the devices from rogue infrastructures.

Each digital certificate has a corresponding Private Key that is held by the device that the certificate represents, and is used as part of the process to prove the identity of that device. Digital certificates can be freely distributed, but the corresponding Private Key must be stored in a secure manner by the device, or the security is compromised.

A digital certificate is signed by a Certificate Authority (CA). Each Certificate Authority also has a digital certificate which is signed by another CA. This process repeats until a "root" CA is reached. A root CA is a CA that signs its own certificate. As a result, every certificate (except for the root CA certificate) has a chain of CA certificates associated with it. This chain of trust, provided by the Public Key Infrastructure (PKI), is what allows a web browser to trace the authenticity of a web site all the way back to a well known authority such as VeriSign without any intervention by the user.

Medical Grade Wireless Infrastructure

When a World Wide Web user connects to a web site on the Internet, a vast number of services provided by the Internet are available. These services include Domain Name Service (DNS), which translates easy to remember domain names into numeric IP addresses, as well as all the PKI sites and services necessary to verify the chain of trust provided by digital certificates.

However, most wireless infrastructures in the hospital are heavily or even completely isolated from the Internet. These networks must function robustly in this much more isolated and independent environment. Where a certificate for a web site associates the web site name (translated by DNS) with a company name (recognized by the Certificate Authority), these same services need to be provided by the wireless system components if they are to be used in a virtually isolated Medical Grade Wireless Infrastructure.

The IEEE standard 802.11i, commonly referred to as WPA and WPA2, provides a framework for authenticating wireless devices using certificates and other mechanisms such as shared secret keys. This framework includes the concept of a Radius Server, which supports a variety of authentication methods, and keeps a database of the keys and certificates that are recognized by the administrators of a given site. A wireless device attempting to access the network encapsulates an authentication request to the Radius Server in a protocol called Extensible Authentication Protocol (EAP).

Authentication mechanisms supported by Devices and the Radius Server are known by their "EAP types". Of particular interest to a Medical Grade Wireless Infrastructure are the three EAP types that support bidirectional authentication for both the infrastructure and client (device) sides using certificates. These are: EAP-TLS, EAP-PEAP, and EAP-TTLS.

In addition, the MDWA also supports legacy authentication mechanisms such as Pre-Shared Key (PSK) and WEP with long and short keys.

Device Certificates

Medical Devices that contain the MDWA use certificates to authenticate the device to the Wireless Infrastructure. The MDWA stores and uses two distinct certificates for authenticating the device, the "OEM" Certificate, and the "Customer" Certificate. In addition, there is a third certificate installed on the device by the manufacture which is used by the Web Server to set up an encrypted link with a Web Browser.

Device OEM Certificate

The OEM Certificate is installed by the manufacturer of the completed host Device and one-time installation of the matching server side certificate on the end-user's Radius server is required.

On the server-side, use of the Device OEM certificate provides "Out of Box" operation of all the MDWA-equipped Host Devices with no site configuration of the Host Device.

Device Customer Certificate

Some sites may wish to manage their own certificate hierarchy. These customers can accomplish this by installing a Customer Certificate on the Host Device that contains the MDWA, rather than using the OEM Certificate provided by the manufacturer.

If a Customer Certificate is installed, then authentication will be attempted with both the Customer Certificate and the OEM Certificate. The reason for attempting to use both is that a customer could easily lock themselves and the manufacturer out of a device if only the Customer Certificate were to be used. Customer sites that deploy their own certificates do not need to install the OEM Server side Certificates on their infrastructure, so only the Customer Certificate will authenticate successfully. The last certificate to successfully authenticate will be marked internally on the MDWA and tried first on subsequent authentications. This avoids any performance penalty associated with trying to authenticate using two different certificates.

Web Server Certificate

A third certificate installed on the device by the manufacture is used by the Web Server. This Web Server is used for configuring and managing updates to the Wireless Card.

The Web Server Certificate and its corresponding private key are kept on the MDWA. These are used to authenticate the MDWA to a Web Browser that is accessing the administration interface on the MDWA. This certificate and associated private key are also used as seed information to set up the Secure Socket Layer (SSL) connection between the MDWA and the Web Browser.

Device Certificate Chains

Since the MDWA might not have access to any Certificate Authority on the Internet during authentication, it must store the entire certificate chain used to verify the Wireless Infrastructure's certificate. The MDWA supports two distinct certificate chains for authenticating the infrastructure, the "OEM" Chain, and the "Customer" Chain. There will normally be multiple certificates in each of these certificate chains.

Server Certificates and Chains

The 802.11 Authentication Server Certificate and its corresponding private key are kept on the 802.1x authentication server. This certificate is used to authenticate the Wireless Infrastructure to the MDWA. The Certificate Authority (CA) certificate chain is used to sign and validate the various certificates.

Provisioning of Certificates and Certificate Chains

The OEM certificate chain is written to the flash memory on the MDWA during the provisioning process. When the MDWA boots, it checks if this area has new data. If so, the area in flash memory is copied or converted to a format that can be used directly by the supplicant. All the certificates in the certificate chain are concatenated into a single PEM format file with the root certificate at the beginning of the file.

During the provisioning process, a device certificate and private key is written to an area in the flash memory. Like the OEM chain, this OEM device certificate and private key are converted into a form (PKCS #12) that can be used directly by the supplicant. The encryption key for the PKCS #12 envelope is also written to flash and converted to a form that is useable by the supplicant. The MDWA software uses this key to decrypt the PKCS #12 envelope and extract the private key.

Contents and Format of the Device Certificates

The device certificate contains the MAC address in the Canonical Name (CN) section of the certificate.

The device certificate and corresponding private key are generated outside the MDWA during the provisioning process. The device certificate is signed by a self signed or traceable Certificate Authority. Then the device certificate and private key are packaged into an encrypted PKCS #12 envelope. The OEM device certificate and key are installed on the MDWA at provisioning time. If the customer wishes to install their own device certificate and key, the PKCS #12 envelope and the password to decrypt it will be uploaded to the MDWA through the web administration interface.

Committed Bandwidth

Many medical devices use a dedicated and/or proprietary network as a method to provide dedicated bandwidth, resulting in a high probability of packet transmission success. Each dedicated/proprietary network adds cost for the hospital. A preferred implementation is that the many medical devices can share a single network. Experience with the WMTS experiment for the last 7 years indicates that competing manufacturers are not capable of creating solutions that work together in the absence of a standard. However, for the network to be shared, both the network and the clients that require a committed bandwidth on the network must support the same method for allocating and sharing bandwidth. Bandwidth allocation and prioritization such as that provided by the 802.11e QoS standard can support and enable a pre-allocation of a committed bandwidth in support of the real-time vital signs data (and other high priority data), so that other applications that share the infrastructure can do so without adversely impacting applications such as vital signs monitoring and alarm reporting. Further, a method for ensuring that the bandwidth is available includes testing the network against the intended use, including all planned network loads. This can be accomplished at installation time using tools such as IxChariot, available from Ixia.

SAR Management (FCC Low Power Exemption)

The FCC limits the amount of Joule heating by a transmitter on portable device (portable devices are defined as those used within 20 cm of the body) averaged over any 6-minute time interval. A typical 802.11 radio exceeds the SAR limits for a patient worn device unless the EIRP (Effective isotropic radiated power, EIRP=Power*Antenna_Gain) is very low. In this case, the transmission distance is severely limited. However, when the transmission protocol restricts the transmit duty cycle, source based averaging can be used. Assuming the transmission protocol limits the duty cycle to 10 percent, then a factor of 0.10 is applied to the SAR level, allowing the radio to have a high EIRP when the transmission occurs, resulting in an improved transmission range. To do this, the radio must provide a measure of the transmission duty cycle. Coupled with a knowledge of the antenna gain and transmit power, this allows the MDWA or Host Device (when the information is sent across the Host API) to implement a protocol that enforces a limit on the SAR. This limit provides support for either meeting the FCC SAR low-power exemption, or simply staying below the SAR limits.

Watch Dog

MDWA failure reports include failures due to latch up, including failure of microprocessor internal watch dog timers. Typical off the shelf radios may latch up and stop transmitting, with no way to alert the host device, resulting in loss of ability to transmit patient alarms. Should a software application or operating system fault occur, the MDWA incorporates an independent watch dog circuit, external to the microprocessor, which provides a means to restart the module, whereupon the MDWA alerts the host device of the reboot via the Host API, and returns the MDWA to a known state.

POST and BIST

One embodiment of the MDWA contains a Power-On Self Test (POST) and a Built-In Self Test (BIST). The POST occurs when the module is first powered up to ensure that the major functions operate correctly, but is bypassed during subsequent transitions out of hibernate mode (where the CPU was powered down), decreasing the power-up time. The BIST can provide a much more extensive set of tests and diagnostics, and may be used both during manufacturing as well as at the customer site to verify correct operation of the module and diagnose any hardware failure. Typical radio cards either report nothing upon start up or a numerical error code that can not be interpreted by the host. The BIST and POST provide diagnostics that are not typically available to the host device.

Software Updates

A MDWA can support updates of the wireless adapter software from the wireless network interface with little or no involvement by the Host Device. The MDWA can automatically download and install the new firmware. Alternately, devices with a user interface and appropriate service screen may trigger the final SW load into the MDWA through that user interface. In another implementation, the MDWA can be designed to load SW from the Network Server on power up or boot or upon other event (such as notification across the Host API) where the MDWA can be sure no patient is being monitored. Enterprise solutions can be used to have an external server push new firmware to the MDWA.

In one embodiment, the MDWA provides the ability for the Network Server to program the card software. By way of example, there are three methods for providing software updates. In the first method, the device overwrites its own firmware in real-time, which poses problems if there is an error in the code load. In a second method, two copies of the firmware can be stored on the device and the power up interrupt can point to either copy. Upon boot failure of a newly loaded version, the boot core can re-boot from the earlier firmware version. The third solution is a compromise between the first two methods, where the new firmware overwrites most, but not all of the original firmware. The boot core, responsible for a few basic operations, including writing new firmware, is left unchanged. In the event the firmware load is corrupt, the boot core is still available to re-load firmware. The second solution requires and the third solution can use a separate bank of memory from that location where code is run. This allows new firmware to be downloaded and the code integrity confirmed before the new firmware is executed. Integrity checks include CRC and revision checks.

The ability to update the MDWA software through the radio interface can allow a network product to update all of the MDWAs on the network, independent of the instrument type or protocol. In one embodiment, updates of the wireless card software are made over the wireless network interface with little or no involvement by the host device. The MDWA software can be supplied by HTTP, FTP, TFTP, SNMP, and other services known to those skilled in the art. The independence of software revisions to instrument type or protocol reduces the complexity of the host device software that needs to be integrated into each instrument and validated.

Typically, anyone with the programming tool can upload new firmware to the card. The preferred embodiment, however, advantageously uses bi-directional authentication to ensure that no one can "hijack" the device and install their own firmware.

While MDWA firmware updates can be accomplished in a device independent manner in one embodiment, in the preferred embodiment, device firmware updates will benefit from some support from the Host Device and associated communications protocol. This protocol allows a confirmation that no critical applications, e.g. continuous vital signs monitors in process, will be interrupted by a MDWA firmware update.

By way of example, for an MDWA embedded in a monitor, firmware updates of the MDWA can be done by either: (a) disassembly of the monitor, (b) loading the MDWA firmware into the monitor, which subsequently re-programs the MDWA or (c) an over-the-air update. Option (a) requires excessive work for each firmware update and option (b) requires custom firmware be written on both the MDWA and Host Device sides. Both require physical access to the Host Device. For these reasons, the preferred embodiment performs firmware updates for the MDWA over a WLAN communications interface. Further, since medical devices are regulated and must have traceability of all device software by serial number, the MDWA can provide the capability to store and export version information for Host Device hardware and software components to the network system. This version information can in turn be used by the system software to determine what software modules or releases are appropriate for the MDWA, the Host Device, and each of the sub-components that make up the Host Device.

In a further embodiment, the MDWA provides a software update to a Host Device by loading new Host Device software, including firmware updates as part of the Host API, from the wireless network. This allows the Host Device to use the MDWA as a staging area for loading firmware updates. That is, the memory that supports firmware upgrades for the MDWA can also be used as a staging area for over-the-air firmware upgrades. The invention includes a Host API that allows the Host Device to use MDWA's memory via any host interface.

Medical device operation cannot be safely interrupted; therefore in one embodiment, the MDWA provides a mechanism via the Host API Proxy and/or inspection of data using Adapter Mode that restricts firmware upgrade activity to only occur when there is no patient activity.

Diversity

Diversity is typically used on reception where the received power of different antenna elements is analyzed, and the element with the highest power is used for RF input. The different antenna elements can easily have a 30 dB performance difference, depending on the constructive/destructive interference at that point in space. This highest power element is assumed to be the best element for transmissions that occur at a time very close to the reception. The MDWA supports one or more antennas, any of which may be disabled for Host Devices that cannot accommodate a second antenna. By way of example, antennas can be oriented to provide polarization and spatial diversity for both the 2.4 and 5 GHz bands. The use of diversity can also be manipulated by the system software, so that the performance of the 802.11 location capabilities can be improved by sending some packets through both antennas, improving the radiation profile to achieve a more isotropic pattern and thus better accuracy for determining the location for systems that use received RF power as an input variable for location determination. A cabled, modular antenna allows for easy disposition of the antenna within an embedded device. In comparison, an antenna that is fixed with respect to the MDWA may be too large in one dimension for inclusion in the host device. A cabled antenna also can allow for an antenna-radio pair with a modular device approval to fit inside multiple embedded devices, where a fixed antenna would not, simplifying regulatory and compliance efforts for the host device development.

In the case where the location beacons are transmitted without any RF reception, it is not obvious which element should be used. In this case, one embodiment of the MDWA system splits power between the two elements, possibly producing a circularly polarized signal. If location beacons are very short and transmitting two beacons, one out each antenna then as in a preferred embodiment, then the beacon is transmitted via antenna 1 and then via antenna 2.

Alternate Channel

Some Real Time Location Services (RTLS) (including location products that can provide a secondary communication system, such as the AeroScout and Radianse systems) can provide a telemetry channel, typically supporting only a small data payload. The MDWA supports such interfaces and can use such systems as an auxiliary telemetry channel. For example, this channel can either be used at all times, enabled as a function of the host's state, or enabled as a function of the 802.11 link state. The data payload can be any state information for the Host Device, including, but not limited to, patient alarm status, a reduced set of physiological data, performance metrics, battery status, host on/off, 802.11 link status, etc.

Mesh Network (Gateway)

The MDWA provides a mesh network capability by acting as a client on one network or channel, an Access Point (AP) on another network or channel, and routing packets between those networks. For example, the MDWA can be an AP on a first network, such as a low power personal area network (PAN), and a station (STA) on a second network, such as an 802.11a/b/g network. The MDWA can route packets between these two networks. These networks could use the same or completely different protocols, including but not limited to 802.11a/b/g, a Personal Area Network including any of the IEEE standards, e.g. 802.15.1 (BlueTooth), 802.15.3 (Ultra Wideband), 802.15.4 (Zigbee), a Metropolitan Area Network such as 802.16 (WiMAX) or HiperMAN, and Wide Area Networks, including cellular. Using one or more of these various types of networks, the MDWA can aggregate vital signs data from one or more sensors directly attached to or worn by the patient, or from one or more applications running on the Wireless adaptor, or a combination thereof. The MDWA can further process that data (or aggregated data) in order to suppress false alarms. Once the data has been processed, the device can then forward the processed and filtered information to another device, e.g. server, PDA, laptop, cellular phone, connected to the wireless infrastructure. We note that for some networks, the concept of routing in the IP sense is not defined. For these networks, the MDWA implements the analogous functionality of taking data to/from devices on a first network and appropriately formatting the data from/to a second network.

Additional Functions

Several of the MDWA 100 functions are now described in more detail. In one embodiment, the MDWA provides two modes of operation. In either mode, the device can be customized to meet the needs of the Host Device and the final application. Parameters can be configured as follows:

The MDWA first provides a method to set modes for default operation, including selection of which host interface to use (USB, Serial, PCMCIA, Ethernet, Card Bus or other interface known to those skilled in the art) and defining the protocol variables, e.g. bit rate, flow control on/off. The host interface to use can be determined automatically, or set once. In another embodiment, auto rate detection algorithms are implemented in addition to setting a default operation mode.

The MDWA further provides a method to set TCP/IP and 802.11 parameters, e.g. configuring for DHCP or Static IP address assignment, and Service Set IDentifiers (SSID).

The MDWA further provides a method to install network applications, such as a web server/client, TFTP server/client, FTP Server/Client, SNMP client, NTP client, 802.1x supplicant, and other network applications familiar to those skilled in the art. These applications provide services for the radio card which the host inherits without having to implement each of these services on the host itself. For Host Devices with memory, CPU, and other constraints, this provides substantial savings.

In one embodiment, a TFTP client is directed to download new firmware for the MDWA and/or the host from a server. A TFTP server is then used to upload the firmware from the MDWA to the host. As those skilled in the art are aware, the same can be accomplished with a web server/client, through FTP, SNMP, and other applications. In addition, an NTP client provides a way for the host to always have an accurate date and time. This is important for time-stamping data and/or debugging, where accurate time stamps allow temporal correlation of data from the client with data from the network.

The MDWA further provides a method to install supplemental applications that increase the functionality of the MDWA to that similar to a conventional medical device. These functions include, but are not limited to, the ability to process, partially process, or aggregate data including, ECG data (including arrhythmia detection); EEG data; $S_pO_2$ data; $CO_2$ data; cardiac output data; and temperature data. In one embodiment, partial processing of data can be used to off-load from the Host Device algorithms for which the Host Device does not have sufficient CPU bandwidth.

In one embodiment, the aggregation of data feature can be used when multiple sensors on various networks are attached to the same patient, for example, when a stand-alone $S_pO_2$ monitor and a stand-alone ECG monitor are used. In this case, knowledge of both data sets allows a more robust interpretation of the patient's condition. Arrhythmia analysis can be augmented by knowledge of the oxygen saturation levels and the trends thereof. For example, a drop in oxygen saturation levels while the heart continues beating normally could indicate a pulmonary problem such as apnea or airway obstruction.

The MDWA further provides a method to configure security parameters. Such parameters include, but are not limited to, installing certificates, setting passwords, and other security configuration settings known to those skilled in the art. Other parameters relate to installing a serial number, and MAC address, applying firmware upgrades, defining the operating parameters for location beacons, and in the case of adapter mode, configuring a discovery protocol.

Diagnosis

Another aspect of the MDWA involves debugging and diagnosis of an MDWA and/or host device or host device API in the field. For example, a remote technical service group could do such debugging if status information is made available over the medical network. A MDWA according to the invention can provide status information including radio performance metrics such as RSSI, retry rates, channel information, Signal-to-noise ratio and version information to a host computer. Such information can be sent over a network via SNMP or other methods known to those skilled in the art. A further embodiment of the MDWA includes functionality to support remote trouble shooting and problem resolution through both interactive and automated diagnostics, such as reporting the results of self tests, of hardware/software compatibility status as well as the results of upgrades and configuration changes. Moreover, the MDWA can provide support for a function to partially or completely restore a factory default configuration.

Roaming

Roaming is defined herein as a circumstance where a device or installation including a MDWA logically changes association status from one AP to another, typically due to physically moving from one location to another, but also due to noise levels, AP loading, and other factors that may make a second AP provide a better communication channel. In one embodiment, the MDWA can support a roaming velocity of at least 5 miles per hour, even with encryption and authentication enabled. (Authentication adds an additional step to the roaming process.) This MDWA can further periodically scan for available Access Points in order to maintain a list of neighboring APs, which allows the MDWA to quickly jump to a new AP in the event the current AP becomes unavailable. The MDWA can use other solutions, such as CCX V2 or greater (Cisco compatibility extensions) or 802.11r in order to populate the AP list. In some applications when a device including a MDWA is out of range, a reduced scan interval can be applied after a timeout in order to reduce power consumption. The reduced power feature can be configured to run automatically or to be set through a Host Interface API.

Additional Uses

Additional embodiments of the MDWA include web servers, enabling MDWA use as: (a) a universal device configurator; (b) virtual display; (c) a broadcasting device for data display on a large screen monitor in the procedure or patient room; (d) a universal device upgrade utility; and (e) as an application server.

In one embodiment, a MDWA can include a web server for use as a universal device configurator. Using the MDWA universal device configurator, medical devices can be configured or re-configured remotely or locally over the internet. Such remote configuration can simplify the proliferation of device configurator applications and the configuration processes.

Additionally, a web server is installed on the WMDA to provide a virtual display of the host device that can be viewed via a web browser. The MDWA application can format and broadcast device data for display on a large screen monitor, such as a Monetron sold by Welch Allyn, Inc. A Monetron is a large screen that is used to collect patient monitor data and display it locally (in the same manner that a central monitoring station might see the data) to enable consulting physicians to see the data. This MDWA embodiment is also enabled to collect and combine data from other sources (devices, EMR) and broadcast for display on a large screen monitor (such as Monetron).

In a further embodiment, a web server is installed on the MDWA to enable the MDWA's use as universal device upgrade utility. The small web server allows a customer and/or service technician to connect to a secure server via a browser and to download and install updated firmware.

In a further embodiment, the web server on the MDWA allows for a customer to license new parameter analysis software that extends the capabilities of the device, and thus the MDWA functions as an application server. The new software can run on the MDWA instead of the device processor. The MDWA application displays the new hybrid data in a browser on a device having a suitable display, or the MDWA can send the displays by wireless connection to a remote monitor, including a large screen monitor.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention. Therefore, it is intended that the invention not be limited to the particular embodiments disclosed as the best mode contemplated for carrying out this invention, but that the invention will include all embodiments falling within the scope and spirit of the appended claims.

We claim:

1. A medical device adaptive module comprising:
a radio section comprising:
two or more wired means for connecting to and exchanging data packets between the adaptive module, a first host medical device and a second host medical device, the first host medical device comprising a peripheral oxygen saturation (SpO$_2$) monitor and the second host medical device comprising an electrocardiogram (ECG) monitor, the data packets comprising at least a first data packet and a second data packet; and
one or more wireless means for exchanging processed data packets between said adaptive module and a network, the processed data packets comprising a processed first data packet and a processed second data packet, each of the processed first data packet and the processed second data packet comprising medical data; and
a CPU block including one or more memory means and integrated support for hosting one or more applications, wherein the one or more applications comprises a medical data application, the medical data application being configured for continuously for a period of time processing each of the data packets by:
receiving first unprocessed data packets from the first and second host medical devices through the one or more wired means, the first unprocessed data packets comprising SpO$_2$ data and ECG data, processing and aggregating medical data contained in the first unprocessed data packets to create the processed first data packet, exchanging the processed first data packet with the network with the one or more wireless means, then receiving, processing and aggregating and exchanging second unprocessed data packets in the same manner as the first unprocessed data packets, wherein the processing and aggregating comprises determining a pulmonary problem based on the SpO$_2$ data and the ECG data received in the first unprocessed data packets, the pulmonary problem comprising apnea or airway obstruction, and sounding an alarm identifying the pulmonary problem.

2. The module of claim 1, wherein the one or more applications comprises a communications application supporting one or more of bi-directional authentication, 802.11i encryption, one or more web servers, a plurality of password/user name combinations, a TCP/IP sockets API proxy, a conversion means from a native device communication protocol to one or more TCP/IP network interfaces, a SNMP server, a FTP server, and a TFTP server.

3. The module of claim 2, wherein said bi-directional authentication follows the Extensible Authentication Protocol.

4. The module of claim 3, wherein said Extensible Authentication Protocol follows the 802.1x standards.

5. The module of claim 2, wherein said bi-directional authentication application is configured to provide certificate management and processing.

6. The module of claim 2, wherein said bi-directional authentication application is configured to provide password management and processing.

7. The module of claim 2, wherein said bi-directional authentication application is configured to work with multiple certificates.

8. The module of claim 2, wherein said web server is a secure server.

9. The module of claim 2, wherein said TCP/IP sockets API proxy is configured to support multiple endpoints.

10. The module of claim 2, wherein said TCP/IP sockets API proxy is configured to simultaneously accept commands and data.

11. The module of claim 2, wherein said conversion means from a native device communication protocol to one or more TCP/IP network interfaces is configured to fulfill communications requirements needed to establish a communication link between a non-networked host device and a network device.

12. A wireless module comprising:
a radio section comprising:
at least two wired means for exchanging data packets between said wireless module, a first host device and a second host device, the first host device comprising a peripheral oxygen saturation (SpO$_2$) monitor and the second host device comprising an electrocardiogram (ECG) monitor, the data packets comprising at least a first data packet and a second data packet, each of the first data packet and the second data packet comprising medical data; and at least one wireless means for exchanging processed data packets between said module and a network, the processed data packets comprising a processed first data packet and a processed second data packet; and a processing block including least one microprocessor, wherein said at least one microprocessor is configured to host at least one application and at least one radio transceiver and in which the wireless module is further configured with at least one interface mode, wherein the at least one application comprises a medical data application, the medical data application being configured for continuously for a period of time processing each of the data packets by:

receiving first unprocessed data packets from the first and second host medical devices through the one or more wired means, the first unprocessed data packets comprising SpO$_2$ data and ECG data, processing and aggregating medical data contained in the first unprocessed data packets to create the processed first data packet, exchanging the processed first data packet with the network with the one or more wireless means, then receiving, processing and aggregating and exchanging second unprocessed data packets in the same manner as the first unprocessed data packets, wherein the processing and aggregating comprises determining a pulmonary problem based on the SpO$_2$ data and the ECG data received in the first unprocessed data packets, the pulmonary problem comprising apnea or airway obstruction.

13. The module of claim 12, wherein the at least one application comprises a communications application having a conversion means from a native device communication protocol to one or more TCP/IP network interfaces.

14. The module of claim 12, wherein the at least one application comprises a communications application having bi-directional authentication.

15. The module of claim 14, wherein said bi-directional authentication follows the Extensible Authentication Protocol.

16. The module of claim 15, wherein the Extensible Authentication Protocol follows the 802.1x standards.

17. The module of claim 14, wherein the bi-directional authentication application is configured to provide certificate management and processing.

18. The module of claim 14, wherein the bi-directional authentication application is configured to provide password management and processing.

* * * * *